United States Patent [19]

Frey et al.

[11] Patent Number: 4,718,914
[45] Date of Patent: Jan. 12, 1988

[54] METAL BONE IMPLANT

[75] Inventors: Otto Frey; Manfred Semlitsch, both of Winterthur, Switzerland

[73] Assignee: Sulzer Brothers Limited, Winterthur, Switzerland

[21] Appl. No.: 821,399

[22] Filed: Jan. 22, 1986

[30] Foreign Application Priority Data

Feb. 7, 1985 [CH] Switzerland .............................. 558/85

[51] Int. Cl.⁴ .......................... A61F 2/36; A61F 2/34; A61F 2/28
[52] U.S. Cl. ........................................ 623/23; 623/16; 623/22
[58] Field of Search ....................... 623/23, 22, 16, 17; 128/92 Y, 92 YZ, 92 YY, 92 YK, 92 YW, 92 YV, 92 YT, 92 YS

[56] References Cited

U.S. PATENT DOCUMENTS 3,064,645 11/1962 Ficat et al. .............................. 623/23

OTHER PUBLICATIONS

Swanson et al., *The Scientific Basis of Joint Replacement*, Pitman Medical, 1977.

*Primary Examiner*—Richard J. Apley
*Assistant Examiner*—Alan W. Cannon
*Attorney, Agent, or Firm*—Kenyon & Kenyon

[57] ABSTRACT

The prosthesis consists of a sheet metal shell which is formed of two shell parts or half shells to form a closed hollow body. The thickness of the hollow body is in the range of from 1 to 3 millimeters. In addition, the hollow body may be provided with internal supporting elements to rigidify the shell and/or with a filling of an elastic or plastic material.

17 Claims, 5 Drawing Figures

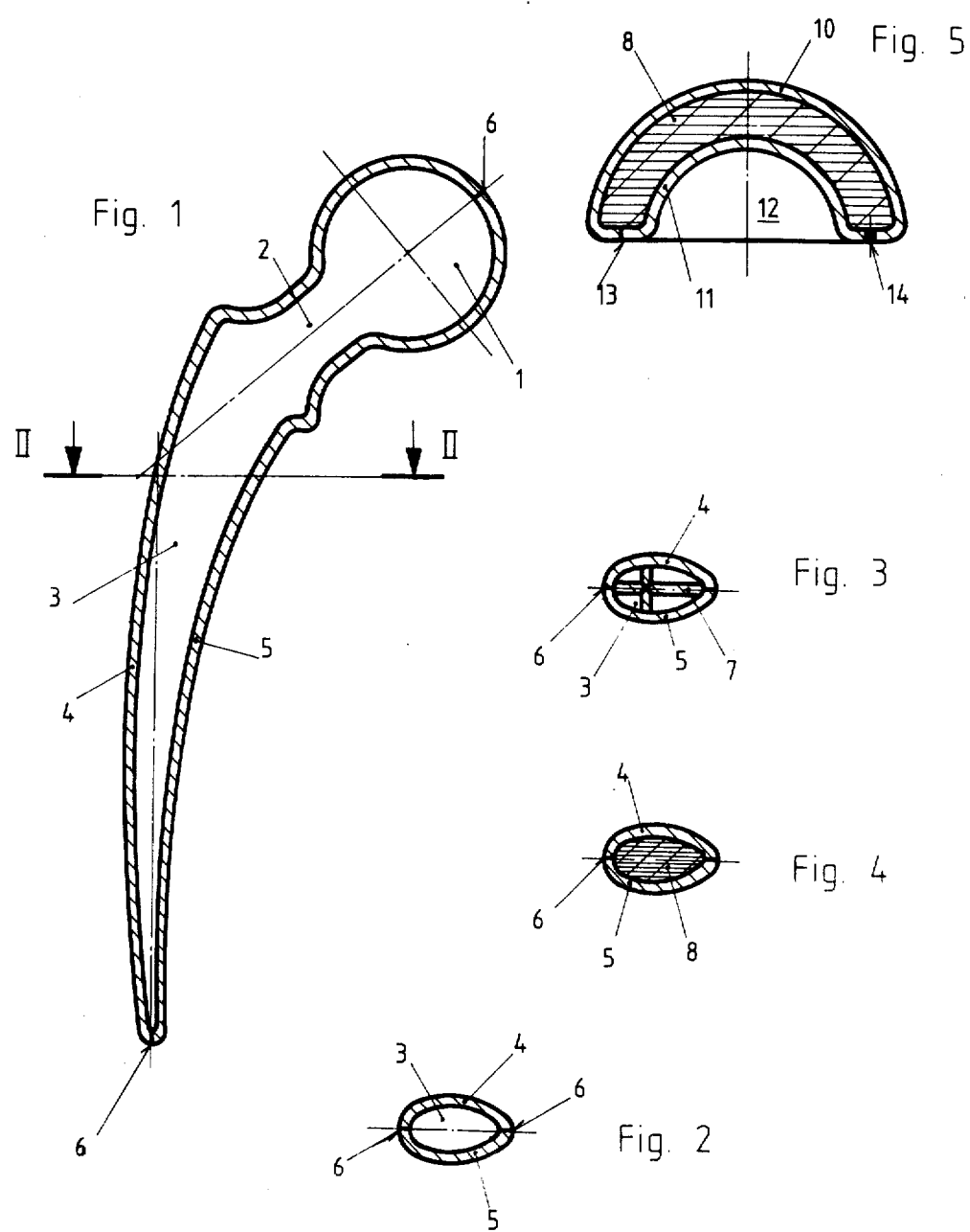

METAL BONE IMPLANT

This invention relates to a metal bone implant. More particularly, this invention relates to a metal bone implant which is at least partially hollow.

Heretofore, it has been known to fabricate prosthesis of various types of metals, usually by casting and machining techniques. However, in order to save weight, especially in the case of joint endoprostheses, it has been known to fabricate such prosthesis at least partially with a hollow portion. Such a construction is described in French patent No. 69318632021313. However, as is the case with the solid prosthesis, the hollow prosthesis have also been made of forged and/or cast parts, the closed hollow body being produced by welding together individual shaped parts. By way of example, U.S. patent application Ser. No. 649,942, filed Sept. 11, 1984 describes a joint head for a femur head prosthesis which consists of a hollow sphere of cast material and a sleeve welded thereto of a forged material.

Generally, the production and machining of the previously known hollow prosthesis have been relatively expensive and complicated, especially if the prosthesis is formed with an anchoring shank having a plurality of ribs thereon.

Accordingly, it is an object of the invention to simplify the production of a hollow metal implant without an undue loss in required mechanical properties.

It is another object of the invention to provide a metal bone implant of at least partial hollow construction which can be readily fabricated.

Briefly, the invention provides a metal bone implant having at least in part a sheet-metal shell which defines a substantially rigid closed hollow body with an exterior surface. Further, the shell has a substantially constant wall thickness along the exterior surface which is sufficient to render the shell self-supporting.

The relatively thin sheet-metal shell is provided with a wall thickness, for example, in the range of from 1 to 3 millimeters The sheet-metal thickness necessary for the self-supporting property depends on the form of the shell and on the selected material The sheet-metal shell can be shaped by pressing, pushing or drawing in one operation, even for complicated exterior forms, in such a way that, apart from polishing of joint sliding surfaces, no remachining of the form is necessary.

In one embodiment, a pair of half-shells which are brought together on a plane of symmetry can be welded together along a peripheral seam in the plane of symmetry in order to define a closed hollow body.

The metal bone implant is of relatively minimal weight as compared with previously known implants Should it be necessary to increase the strength of the shell body, especially to bending loads, one or more supporting elements may be provided internally of the body in order to rigidify the shell. In this regard, the shell may have a relatively complicated exterior surface while the supoorting element or elements may have a simple geometric shape on the interior of the closed body. Further, the hollow body may be filled with an elastic material, for example of an epoxy resin or a silicone rubber, the volume of which is at least substantially invariable.

In order to improve the rigidity of the hollow body by other fillings, use may be made of light-weight materials of high rigidity such as polyethylene, and the like.

The implant may be made of any suitable metal which is known in the implant part from which sheets of the defined wall thickness can be produced with sufficient strength for the purposes intended. Preferably, use is made of a super plastic material, such as alfa/beta titanium alloy.

These and other objects and advantages of the invention will become more apparent from the following detailed description taken in conjunction with the accompany drawings wherein:

FIG. 1 illustrates a longitudinal sectional view through a femur head prosthesis constructed in accordance with the invention;

FIG. 2 illustrates a view taken on line II—II of FIG. 1;

FIG. 3 illustrates a modified cross sectional view of the prosthesis of FIG. 1;

FIG. 4 illustrates a further modified cross sectional view of the prosthesis of FIG. 1; and FIG. 5 illustrates a cross-section view through an artificial hip joint socket constructed in accordance with the invention.

Referring to FIG. 1, the metal bone implant is constructed in the form of a femur head prosthesis having a joint head 1, a prosthesis neck 2 and an anchoring shank 3. The implant is formed of two half-shells 4, 5 each of which is produced by one of the known sheet-metal deformation methods. In this regard, each half-shell 4, 5 has a substantially constant wall thickness which is in the range of from 1 to 3 millimeters.

The two, half-shells 4, 5 are joined along an "equatorial" circumference by a peripheral weld seam 6 in order to form a closed hollow body. As indicated in FIG. 1, the two half-shells 4, 5 are not symmetrical with respect to each other but may have differently contoured exterior surfaces. Of course, the parts forming the joint head 1 are substantially symmetrical to each other.

The half-shells 4, 5 may be made in anv suitable metal or metal alloy material which is customary in the implant art and which can be processed to a sheet of sufficient strength for the purposes intended. Depending upon the material, the wall thickness may be greater or less in the above-noted range in order to render the prosthesis self-supporting. That is, the stronger the metal, the thinner the thickness.

Referring to FIG. 3, depending on the requirements for achieving increased strength, the interior of the shell body may be wholly or partially filled with a supporting element 7 which is made, for example of bars of the same material which are joined to form a cross. As far as fabrication permits, the bars may be joined with at least one of the half-shells 4, 5 metallurgically before the half-shells are joined together to form the hollow body.

Referring to FIG. 4, as an alternative to improving the strength of the implant, and especially the bending strength, the interior of the shell may be filled wholly or partially with an elastic or plastic material 8 which is stable in volume and capable of displacement. For example, thermosetting plastics which remain viscous or gel-like, for example, epoxy resins or silicone rubber, may be used. The filling of the interior of the body may be carried out to advantage in the region of the weld seam 6 through one or more bores (not shown) which are subsequentially closed, for example with welding material.

Naturally, it is possible to employ both techniques of "filling" the interior of the shell jointly. In this case, the supporting element 7 may be provided with passage openings (not shown) for introducting the flowable media.

Referring to FIG. 5, the metal bone implant is in the form of a hip joint socket which is composed of two half-shells 10, 11. As indicated, one shell 10 forms the outer surface of the socket while the other half-shell 11 forms the actual socket cavity 12 for the uptake of a prosthesis joint head (not shown). The two half-shells 10, 11 are welded together along a peripheral seam 13 which is provided in the center of the equitorial ring area of the socket body. Alternatively, the seam 13 may be located at another suitable point on the circumference of the socket.

As above, the interior of the closed body formed by the two half-shells 10, 11 may be filled with a olastic filling 15 which, in this case, consists of a light material of high rigidity, for example of polyethylene and the like. This plastic material may be pressed in through a bore 14 which is subsequently closed by a plug of welding material.

The invention thus provides a metal bone implant which is made at least in part of a sheet metal construction having a closed hollow body with sufficient strength and rigidity so as to be self-supporting. Such an implant can be fabricated using relatively simple techniques without requiring complicated and expensive machining procedures.

The invention also permits the manufacture of metal bone implants of complicated exterior shapes while at the same time providing a light-weight structure.

What is claimed is:

1. A metal bone implant having at least in part a sheet-metal shell defining a substantially rigid closed hollow body with an exterior surface, said shell having a substantially constant wall thickness along said surface and sufficient to render said shell self-supporting.

2. A metal bone implant as set forth in claim 1 wherein said wall thickness is in the range of from 1 to 3 millimeters.

3. A metal bone implant as set forth in claim 2 which further includes at least one supporting element internally of said body to rigidify said shell.

4. A metal bone implant as set forth in claim 3 which further includes an elastic material filling said hollow body.

5. A metal bone implant as set forth in claim 4 wherein said shell is made of a superplastic material.

6. A metal bone implant as set forth in claim 1 which further includes at least one supporting element internally of said body to rigidify said shell.

7. A metal bone implant as set forth in claim 1 which further includes an elastic material filling said hollow body.

8. A metal bone implant having a pair of sheet metal parts secured together along a peripheral seam to define a substantially rigid closed hollow body with a contoured exterior surface, said body having a substantially constant wall thickness sufficient to render said body self-supporting.

9. A metal bone implant as set forth in claim 8 wherein said wall thickness is in the range of from 1 to 3 millimeters.

10. A metal bone implant as set forth in claim 8 which further includes an elastic material filling said hollow body.

11. A metal bone implant as set forth in claim 8 wherein each said part is made of a alpha/beta titanium alloy.

12. A metal bone implant as set forth in claim 8 wherein said parts define a joint head, a neck extending from said joint head and a shank extending from said neck to form a femur head prosthesis.

13. A metal bone implant as set forth in claim 8 wherein one of said parts is disposed within the other of said parts and forms a socket cavity and said other part forms an outer surface for a hip joint socket.

14. A femur head prosthesis having a pair of sheet-metal shells joined together to define a substantially rigid closed hollow body with an exterior surface defining a joint head, a neck extending from said joint head and a shank extending from said neck, said shells having a substantially constant wall thickness along said surface.

15. A femur head prosthesis as set forth in claim 14 wherein said wall thickness is in the range of from 1 to 3 millimeters.

16. A femur head prosthesis as set forth in claim 14 which further includes at least one supporting element internally of said body to rigidify said shell.

17. A femur head prosthesis as set forth in claim 14 which further includes an elastic material filling said hollow body.

* * * * *

UNITED STATES PATENT AND TRADEMARK OFFICE
CERTIFICATE OF CORRECTION

PATENT NO. : 4,718,914
DATED : January 12, 1988
INVENTOR(S) : Otto Frey, et al

It is certified that error appears in the above-identified patent and that said Letters Patent is hereby corrected as shown below:

```
Column 1, line 13 "2021313" should be -(2021313)-
Column 1, lines 7, 11, 14 and 23 "prosthesis" should be
     -prostheses-
Column 2, lines 9 and 10 "accompany" should be -accompanying-
Column 2, line 39 "anv" should by -any-
Column 3, line 2 "introducting" should be -introducing-
Column 3, line 17 "olastic" should be -plastic-
```

Signed and Sealed this

Twenty-eighth Day of June, 1988

Attest:

DONALD J. QUIGG

Attesting Officer

Commissioner of Patents and Trademarks